US010434339B2

United States Patent
Pencea et al.

(10) Patent No.: US 10,434,339 B2
(45) Date of Patent: Oct. 8, 2019

(54) RADIOTHERAPY DOSE DISTRIBUTION MEASUREMENT

(71) Applicant: Elekta AB (Publ), Stockholm (SE)

(72) Inventors: Corneliu Stefan Pencea, Decatur, GA (US); Janus Harasimowicz, Surrey (GB); Nikolas Marinos, West Sussex (GB); Julian Peter David Byrne, West Sussex (GB)

(73) Assignee: ELEKTA AB (PUBL), Stockholm (SE)

( * ) Notice: Subject to any disclaimer, the term of this patent is extended or adjusted under 35 U.S.C. 154(b) by 22 days.

(21) Appl. No.: 15/785,344

(22) Filed: Oct. 16, 2017

(65) Prior Publication Data

US 2018/0117361 A1    May 3, 2018

(30) Foreign Application Priority Data

Oct. 31, 2016   (GB) .................................. 1618326.1

(51) Int. Cl.
| | | |
|---|---|---|
| *G01D 18/00* | (2006.01) | |
| *A61N 5/10* | (2006.01) | |
| *G01T 1/29* | (2006.01) | |

(52) U.S. Cl.
CPC ......... *A61N 5/1075* (2013.01); *A61N 5/1081* (2013.01); *G01T 1/29* (2013.01);
(Continued)

(58) Field of Classification Search
CPC ...................... G06T 5/003; G06T 2207/10116; G01T 1/169
See application file for complete search history.

(56) References Cited

U.S. PATENT DOCUMENTS

| | | | |
|---|---|---|---|
| 5,357,805 A | 10/1994 | Fujimoto et al. | |
| 6,207,952 B1 * | 3/2001 | Kan ..................... | A61N 5/1048 250/252.1 |

(Continued)

FOREIGN PATENT DOCUMENTS

| | | |
|---|---|---|
| EP | 2148222 A1 | 1/2010 |
| JP | 2004 129678 | 4/2004 |

OTHER PUBLICATIONS

Search Report under Section 17 for United Kingdom Patent Application No. 1618326.1 from Intellectual Property Office of the United Kingdom, dated Apr. 25, 2017.

(Continued)

*Primary Examiner* — Kiho Kim
(74) *Attorney, Agent, or Firm* — Finnegan, Henderson, Farabow, Garrett & Dunner LLP

(57) ABSTRACT

A method for measurement of dose distribution in a radiotherapy apparatus includes providing a detector holder situated at least partially within a tank, the detector holder comprising a radio-opaque marker and a visual reference point, the marker and the reference point being separated and in a fixed spatial relationship to each other; locating the tank within a bore of the radiotherapy apparatus; rotating a gantry and monitoring the position of the detector holder with an imaging apparatus; vertically displacing the detector holder until the reference point is positioned at a desired level, and adding liquid to or removing liquid from the tank until the surface of the liquid is level with the reference point. Features of the detector holder and tank are also described.

14 Claims, 5 Drawing Sheets

(52) U.S. Cl.
 CPC .......... *A61N 2005/1054* (2013.01); *A61N 2005/1055* (2013.01); *A61N 2005/1076* (2013.01)

(56) References Cited

U.S. PATENT DOCUMENTS

| | | |
|---|---|---|
| 8,321,179 B2 | 11/2012 | Simon et al. |
| 2007/0014928 A1* | 1/2007 | Delaperriere ........... G01T 1/169 427/372.2 |
| 2008/0164416 A1* | 7/2008 | Safai ....................... G01T 1/202 250/366 |
| 2013/0287170 A1 | 10/2013 | Ebstein |
| 2014/0054465 A1 | 2/2014 | Berke |
| 2015/0036141 A1* | 2/2015 | Adamovics ........... A61B 5/0073 356/432 |
| 2015/0343241 A1* | 12/2015 | Han ..................... A61N 5/1075 378/205 |
| 2016/0008631 A1 | 1/2016 | Harada et al. |

OTHER PUBLICATIONS

Smit, K. et al., "Relative dosimery in a 1.5 T magnetic field: an MR-linac compatible prototype scanning water phantom" IOP Science, pp. 4099-4109.

* cited by examiner

RADIOTHERAPY DOSE DISTRIBUTION MEASUREMENT

CROSS-REFERENCE TO RELATED PATENT APPLICATIONS

This application claims the benefit and priority of prior United Kingdom Patent Application No. 1618326.1, filed on Oct. 31, 2016, the entire contents of which are incorporated by reference herein.

BACKGROUND

Field of the Invention

The present invention relates to techniques for the measurement of radiotherapeutic dose distribution in radiation therapy apparatus, particularly but not exclusively in Magnetic Resonance (MR)-guided linear accelerator apparatus.

Background Art

Radiotherapeutic apparatus is well-known, in which a source of radiation emits a beam of radiation that is directed toward a patient in order to destroy or otherwise harm cancerous cells within the patient. It is normal to collimate the beam so as to limit its spatial extent to a desired region within the patient (usually the tumour containing the cancerous cells or a sub-section of the tumour) and to avoid irradiating nearby healthy and/or sensitive tissue. The source can be a linear accelerator (linac) for high-energy (MV) X-radiation, or an isotopic source such as Co-60. The source is normally mounted on a rotatable gantry, so it can be rotated around the patient in order to irradiate the desired region from a number of different directions, thereby reducing the dose applied to healthy tissue outside the desired region. The collimator can move to change the shape of the beam as the source rotates, in order to build up a complex dose distribution for tumours with more challenging shapes and/or which are located near to sensitive areas. An electronic portal imaging device (EPID) may be mounted to the gantry on the opposite side to the source so as to receive the beam once it has been attenuated by passage through the patient; this device produces an image which can be used for correctly aligning or calibrating the system, as well as for assessing the patient's location and the placement of the radiotherapeutic treatment.

Incorporating real-time image guidance into radiotherapy can improve tumour targeting accuracy, enabling better avoidance of critical structures and reducing side effects. Such guidance is of particular benefit if a non-ionizing imaging technique such as MRI (magnetic resonance imaging) is employed. Currently effort is being put into integrating a linear accelerator with an MR scanner; integrating high-quality MRI with a linear accelerator (creating a "MR Linac", or MRL) allows tissue to be tracked online, and therapeutic radiation beams can be guided to their targets (which may be moving and deforming, such as when the patient breathes) with sub-millimeter precision during treatment.

With the requirement for precision in applying therapeutic radiation comes a requirement to be able to model and characterise the characteristics of the beam of therapeutic radiation as it passes through the body of the patient, and to determine the radiation dose distribution within the patient's body, taking account of attenuation of the radiation beam as it passes through bodily tissue. This cannot be performed on a living patient because it would risk applying an excessive dose of radiation, and it would be difficult to carry out in solid tissue, so it is usually carried out by submerging a waterproof detector in a tank full of distilled water. The detector is moved in three dimensions covering the full radiation field width and length at depths which reach several tens of centimeters. Water is chosen not only because is the closest in physical density to human tissue but it is also consistently homogeneous and relatively cheap. The detector is mounted to a three dimensional moving mechanism that moves the detector in three orthogonal directions within the water in the tank, to different positions under the radiation beam so as to measure the dose distribution at those positions.

When carrying this out on linear accelerator apparatus, a water tank is placed on an adjustable platform and it is aligned to the radiation beam using room lasers (lasers provided in the room in which the radiotherapy apparatus is located specifically for alignment and calibration purposes) and a light field which shines through the collimator aperture to mimic the radiation field. The tank is filled with water to the level indicated by an optical distance indicator (ODI) which shows how far below the radiation source an object is. Finally, the detector is aligned to the centre of the radiation field at the surface of the water by the moving mechanism (which is mounted to outside of the tank). For measuring dose distribution, the radiation beam is directed downwardly into the tank and the tank is filled to various depths, in order to take measurements equivalent to the radiation passing through various amounts/depths of human body tissue. For each fill level, the detector is moved to a number of different locations in order to build up a profile of how the radiation beam deposits dose in water in the tank, which can then be extrapolated so as to give the dose distribution within the body of a patient. In order to measure the depth to which the tank is filled, a piece of paper or other reflective material is placed on the surface of the water. This reflects the light shone on to it from the ODI and field light, allowing the position of the surface of the water to be measured.

In these known processes the final measurements are inherently inaccurate: firstly, the placement of the tank is performed by aligning by eye with laser pointers; secondly, the depth of the water is determined by visual inspection of an ODI reading from a piece of paper floating on the water surface (visual inspection is inherently inaccurate, and takes no account of surface tension and wetting effects on the paper), and thirdly, these visual alignments are merely surrogates for the position of the radiation beam, which is what needs to be measured. Therefore, there is a need for a more accurate way of measuring the beam profile of a radiotherapy machine.

There are additional problems where the radiotherapy apparatus is an MRL, having a cylindrical or near-cylindrical bore in which the patient is positioned for therapy (usually the bore is not much bigger than it needs to be to accept an averagely-sized patient, who may have temporary frames or other fittings attached so as to be able accurately to place a particular anatomical part or region within the bore), or any apparatus where space is tight and visibility difficult. Because the MRL radiotherapy beam isocentre is in the middle of a bore of about 1-2 m in length and no more than about 1-1.5 m in diameter, the physical space for a water tank is very limited, and the conventional tanks used in a linac are unsuitably large (usually these tanks are rectangular, like a large fish tank, with walls of radiation-transparent material of constant thickness, and with their height being equal to or greater than the maximum frontto-rear measurement of a typical patient and their width being equal to or greater than the maximum side-to-side measurement of a typical patient); because the moving mechanism is mounted to the outside of the tank, this means that the maximum size of the tank is limited, and so is the range through which the mechanism can move the detector, to the extent that dose distribution measurements cannot be taken at every position within the bore. It is not possible to use lasers for aligning the tank or an ODI for measuring the surface of the water because there is no line-of-sight available, this being blocked by the magnet coils surrounding the bore. Therefore there is a need for a dose distribution measurement system which can be aligned without the need for optical aids, which has an increased positional accuracy with respect to the radiation isocentre (the term "isocentre" used herein means, for any rotational position of the source, the point on the plane in which the beam is rotated by the gantry which intersects with the instantaneous axis of rotation of the source (i.e. the axis of rotation of the source at that rotational position)).

SUMMARY OF THE INVENTION

The present invention is predicated on the realisation that the constraints of the bore size in typical MRLs or Positron Emission Tomography (PET) apparatuses, and of the typical field width in such apparatuses (about 57 cm in an MRL) render a typical water tank and three dimensional radiation detector movement mechanism unsuitable, but that if dose measurements are taken in more than just the vertical direction, such as in both the vertical and horizontal directions, the alignment accuracy and the precision of dose distribution measurement and radiation beam characterisation can be improved, and that this is further improved if a tank is used which is shorter and wider compared with conventional tanks.

The present invention therefore provides a method for the measurement of dose distribution in radiotherapy apparatus comprising an apparatus for generating a beam of therapeutic radiation and an imaging apparatus, one or both apparatuses being mounted to a rotatable gantry adapted in use to rotate around a bore of the radiotherapy apparatus and around an isocentre therein, the method comprising: a) placing a detector holder within a tank, the detector holder comprising a radio-opaque marker and a visual reference point, the marker and the reference point being separated and in a fixed spatial relationship to each other, and the tank in use containing a liquid having a surface level vertically uppermost; b) locating the tank within the bore such that the detector holder is in the vicinity of the isocentre; c) rotating the gantry and monitoring the detector holder using the imaging apparatus to determine the position of the marker relative to the isocentre, and moving the detector holder so that the marker is at the isocentre; d) displacing the detector holder vertically [while monitoring its position relative to the isocentre using the imaging apparatus to detect the marker] such that the reference point is positioned at a point level with a desired surface level of the liquid, and e) adding liquid to or removing liquid from the tank until the surface of the liquid is at the same level as the reference point.

Such a method is easily carried out when the tank is positioned within the bore; even though it is not possible see the tank other than by looking along the length of the bore, the surface of the liquid in the tank is clearly visible (though a window in the end wall of the tank, or through the tank end wall if it is formed of a transparent material), and the reference point (for example a pointer with a sharp tip) is also clearly visible. Providing a bright light from the other end of the bore can increase visibility. Water can be added or removed through a pipe provided at a corner of the tank, thus not obscuring the surface of the liquid and the reference point from view.

The tank can be placed on the patient support, which is able to move into and out of the bore in parallel with its axis. Before or after the level of the water is set as described above, the tank may be aligned relative to the isocentre using the imaging apparatus to monitor a fiducial phantom on or in the tank as the tank is moved relative to the bore; this ensures that the side walls of the tank are aligned square to the edges of the radiation beam. The term "fiducial phantom" used herein means a device used for determining beam geometries which incorporates a plurality of markers (usually at least 4) which are visible to the particular imaging device and the associated radiation used to illuminate the device. These markers could be similar to those described in our co-pending British patent application, No. GB1305751.8, and the phantom could be symmetric or non-symmetric, similar to those described in our co-pending British patent application, No. GB1318958.4. Movement of the tank into and out of the bore may be by means of the patient support. Movement of the tank within the bore in two transverse directions perpendicular to the bore axis, and around the vertical axis, may be carried out using a platform which sits between the tank and the patient support, with movement being actuated by levers which protrude from the platform, so that an operator may reach them by reaching into the bore.

The detector holder may comprise at least one detector for measuring the radiation originating from the radiotherapeutic apparatus, and the method may further comprise moving the detector holder and taking a plurality of radiation dose measurements at different locations within the water in the tank whilst the radiotherapeutic apparatus emits radiation in a first, substantially vertical direction. This is a known process when measuring radiation dose distribution in a radiotherapy apparatus without the restrictions of an MRL (such as a linac apparatus). The method may further comprise moving the gantry to a second rotary position, and moving the detector holder and taking a further plurality of radiation dose measurements at different locations within the water in the tank whilst the radiotherapeutic apparatus emits radiation in a second direction from the second rotary position. If the tank is relatively shallow, when the first measurements are taken these may extend over the entire width of the radiation beam but only to a limited depth of water (thus only representative of doses to a certain depth of patient tissue, typically about 15-20 cm); however, by rotating the gantry so that the beam is aligned horizontally, dose distribution measurements can be made up to a depth almost equal to the bore diameter (e.g. up to about 55 cm), albeit over a reduced field or beam area (about 10×10 cm). Thus accurate measurements may be obtained over a greater range of water depths, and over the full width of the beam at a limited range of depths, and these may be extrapolated so as to produce a full range of dose distribution measurements. The degree of extrapolation required in accordance with the invention is significantly reduced compared to conventional methods. Of course, the measurements need not necessarily be made with the radiation beam in the vertical and horizontal directions—though it is computationally easier to arrange the measurements in parallel with the axes of movement of the moving mechanism—it would be sufficient as long as the two directions are different and not parallel.

In a further aspect, the invention also extends to a detector holder for use in the above methods. The detector holder may comprise at least one radiation dose detector, a radio-opaque marker and a visual reference point, the or each detector, the marker and the reference point being in a fixed spatial relationship to each other. In combination with the conventional movement mechanism, this allows the position of the marker to be precisely determined relative to the isocentre and, because the position of the reference point relative to the marker is fixed and known (the "offset"), the marker can be moved to exactly the position for the desired surface level of the water, and then moved vertically by the vertical element of the offset, so that the pointer tip is precisely positioned at the desired surface level. The detector position can also be precisely monitored and controlled using the analogous process, because its position relative to the marker is also fixed and known. The radio-opaque marker can be embedded within the detector holder, which may be formed around the marker. The detector holder can be configured so that the or each detector is releasably mountable to the detector holder. The reference point may be conical, the tip being the point of the cone, or it could be a surface marking on or an edge of the detector holder; it is advantageous if the reference point is arranged so as not to produce surface tension effects which might interfere with the accuracy of setting the water surface level, and also if the reference point is strongly or contrastingly coloured so that it is easily seen in the bore.

The detector holder may comprise two radiation dose detectors which are mounted to the detector holder so that in use they are separated, and/or are at different vertical heights. This allows measurements to be taken over the full extent of the tank without needing to move the moving mechanism over the total volume of the tank, which allows the moving mechanism to be made smaller. To enable this the spatial relationship between the two detectors needs to be such as to ensure there is an effective overlap between detectors, so that at certain positions within the tank a measurement may be taken using either detector (so allowing the accuracy of the detectors to be checked against each other), whilst at other locations (usually near the walls of the tank) measurements may only be taken using one of the detectors.

In another aspect, the invention also extends to a tank for use in the above methods. The height of the tank in the vertical direction may be less than the dimensions of the tank in the plane transverse to the vertical direction; that is, the tank may be broader in the horizontal plane but shallower than conventional tanks. Such a tank will generally contain less liquid when full than would a conventional tank; this means that the process of filling or emptying the tank to a desired level is quicker than with conventional tanks, and that the full tank is lighter and thus easier to move and align than known arrangements.

The tank may have walls extending in the vertical direction which are generally of substantially constant thickness, there being at least a first section of wall which is substantially thinner. Such a "window" reduces radiation attenuation by the wall material when the beam is directed horizontally through the liquid. There may be a second portion of wall which is substantially thinner, the first and second sections being aligned on opposite sides of the tank. This reduces attenuation by the wall material as the beam leaves the tank, and/or allows the beam to be directed from either side. Preferably the tank is formed of optically transparent material, which allows an operator to check visually where elements of the apparatus are located within the tank.

BRIEF DESCRIPTION OF THE DRAWINGS

The invention will now be described by way of example and with reference to the accompanying figures, in which;

FIG. 3b is an enlarged schematic view of the detector holder of FIG. 3a;

DETAILED DESCRIPTION OF THE EMBODIMENTS

Figure 1A:
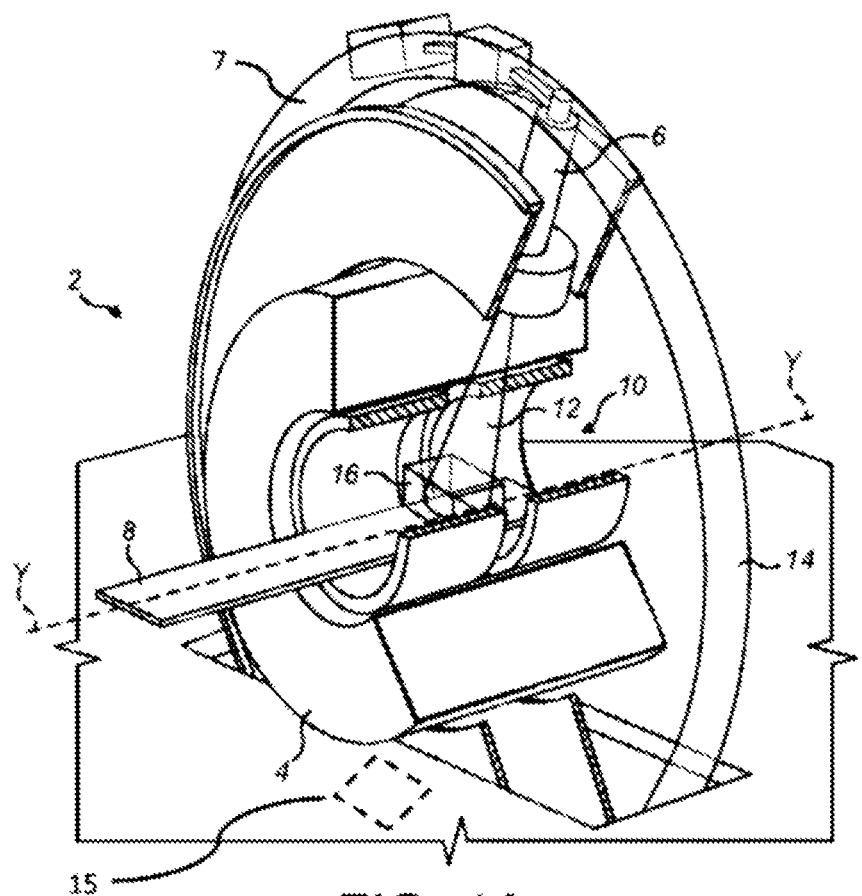
FIG. 1a is a schematic view in partial cross-section of an MRL apparatus showing in outline a water tank for measuring dose distribution.
Figure 1B:
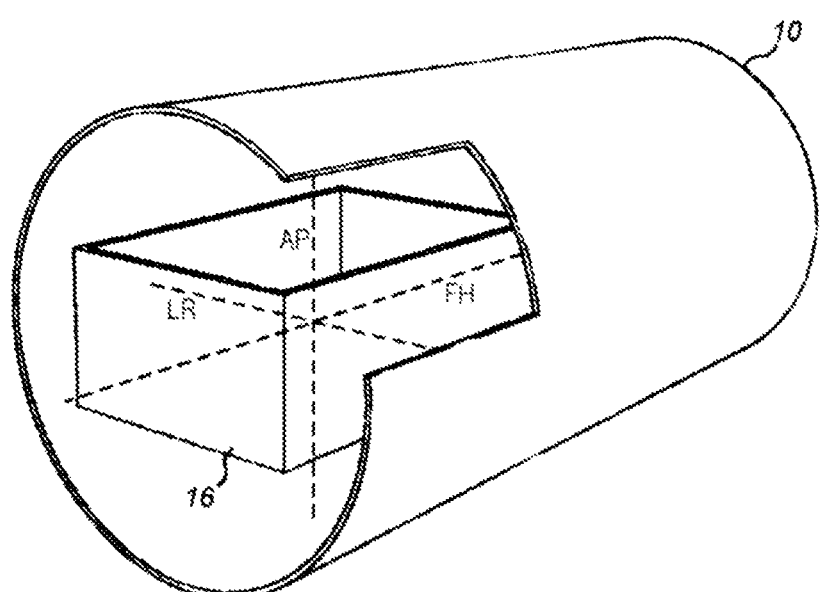
FIG. 1b is an illustration showing the axes of movement within the bore.

FIG. 1 shows a system 2 comprising a radiotherapy apparatus 6 and a magnetic resonance imaging (MRI) apparatus 4. The system includes a couch 8, for supporting a patient in the bore 10 of the system. The couch 10 is movable along a horizontal, translation axis (labelled "Y"), such that a patient resting on the couch may be moved into the bore 10 of the MRI apparatus 4 and into the path of the beam of radiotherapeutic radiation 12 emitted by the radiotherapy apparatus 6. The MRI apparatus 4 is for producing near real-time imaging of a patient positioned on the couch 10. The radiotherapy apparatus 6 is mounted to gantry 7 which in use rotates around the bore 10 along a circular path 14 so as to irradiate a patient from different angles and an EPID 15 (shown in phantom) is mounted on the other side of the gantry 7 to rotate diametrically opposite the radiotherapy apparatus 6 to acquire images once the beam 12 has passed through a patient (or anything else inside the bore and in the path of the beam 12). EPID 15 is used for imaging before and during dose distribution measurement, as will be described below. Operation of the MLC during treatment is well-known, and is described in our earlier European patent application, EP2865419 for example, so other essential elements of the system 2 (such as the beam collimator and the control circuitry which controls the emission of therapeutic radiation from the apparatus 6 and the rotation of the apparatus 6 and the EPID 15, the MR apparatus 4 and the movement of the couch 10) are not described here in detail. For the purposes of dose distribution measurement a water tank 16 is located within the bore 10.

Figure 2:
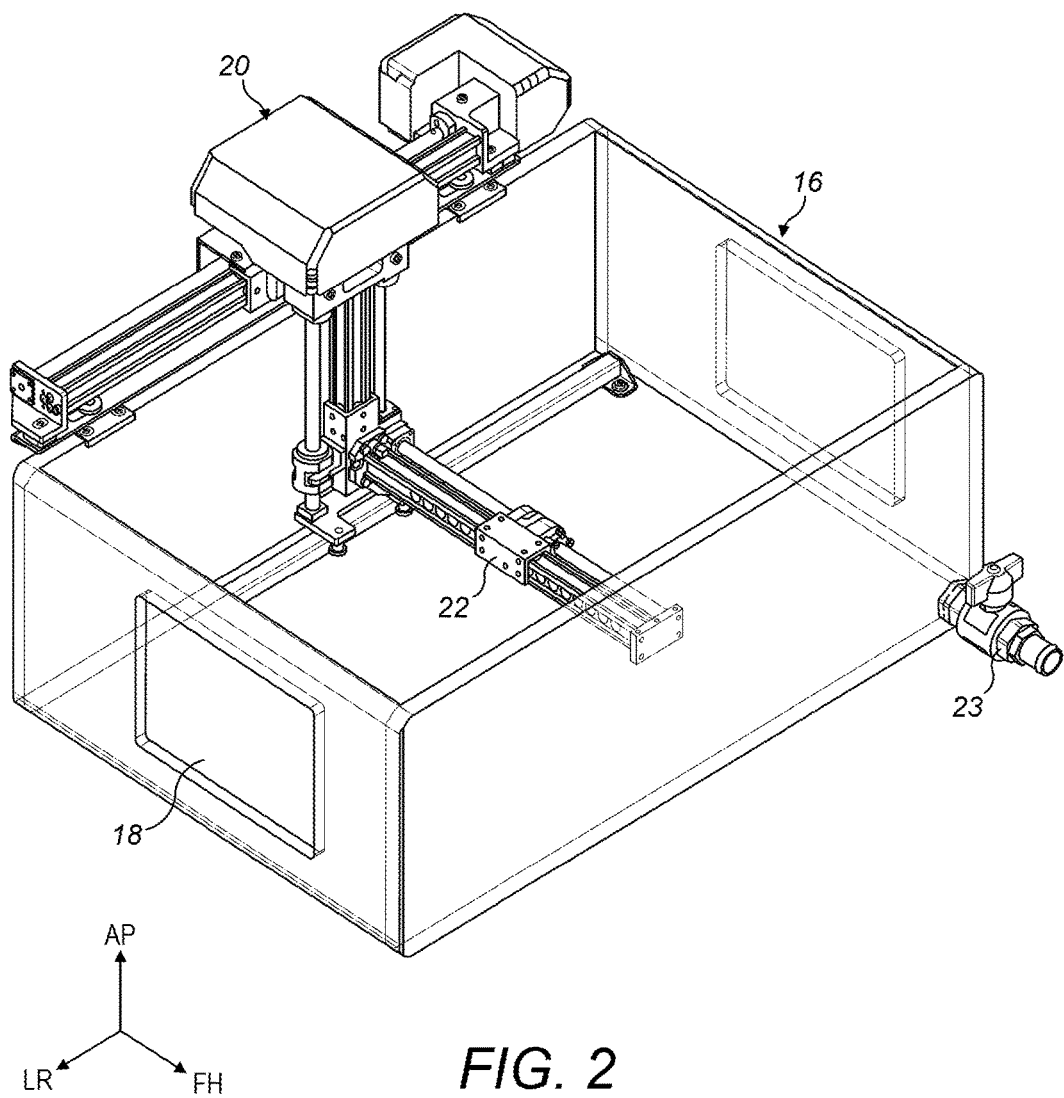
FIG. 2 is a schematic view of a tank according to an aspect of the invention.

FIG. 2 illustrates schematically the bore 10, which is typically cylindrical, about 1 m in diameter and about 2 m long, containing the water tank 16. The drawing shows the orthogonal axes used to reference locations within the bore, which are related to the body of a patient within the bore (not shown): AP denotes the vertical axis (and stands for Anterior-Posterior); FH denotes the axis of the bore (and stands for Feet-Head), and LR denotes the direction transverse to the bore axis (and stands for Left-Right).

FIG. 3 shows the water tank 16 in more detail. It is generally rectangular (about 55 cm square in plan and about 24 cm tall) with an open top and made of a transparent material such as thermoplastic. The walls are generally constant thickness (about 15 mm, the base may be a little thicker, about 20 mm) apart from two "windows" 18 where the thickness is reduced to about 4 mm. These windows 18 reduce attenuation of the beam (which would otherwise affect measurement precision) when the radiotherapeutic beam is fired horizontally through the tank 16 in the LR direction; the windows are aligned on opposite faces of the tank, so that the beam can be fired from either side of the tank. A mechanism 20 provides for precise movement of a detector holder 22 within the tank, along the AP, FH and LR axes; this mechanism is well-known in the art, and is therefore not described further. The tank also has a tap attachment 23 to which a hose (not shown) may be attached for admitting water into the tank 16 or draining water from it. All parts of the tank which are within the bore are MR-compatible and/or are made of materials which are not affected by the strong magnetic field (typically about 1.5 Tesla) the MR apparatus produces.

As can be seen, the mechanism 20 sits on the top rear wall of the tank, and it will be appreciated that at the extremities of movement along the lateral LR axis the part of the mechanism 20a which generates the longitudinal and transverse movement comes close to the internal surface of the bore 10, and thus dictates the maximum size of the tank; making the tank relatively shallow increases the clearance available at these extremities, and allows this mechanism further travel along this axis before the mechanism touches the bore 10. The part 20b of the mechanism which generates the lateral movement is usually (as shown) fixed at one end of the range of movement in this direction, and this affects the size of the tank 16 and how close it can come to the inner surface of the bore 10.

Figure 3A:
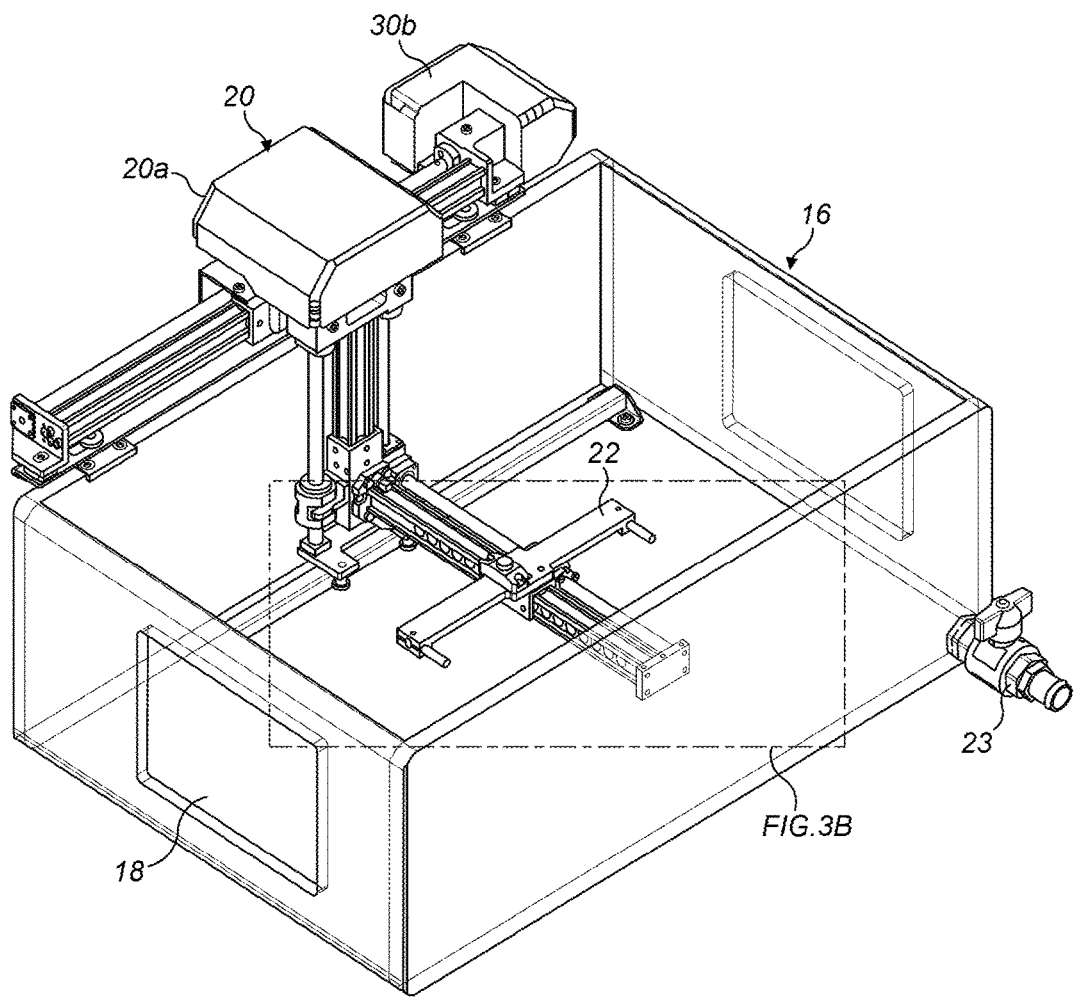
FIG. 3a is a schematic view similar to that of FIG. 2 but showing a detector holder in accordance with another aspect of the invention.
Figure 3B:
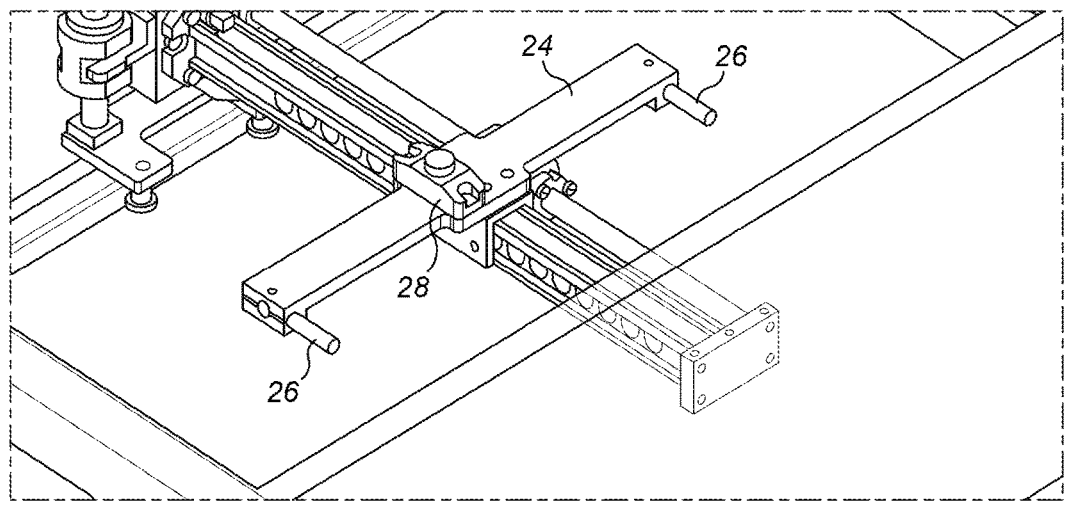
Figure 3C:
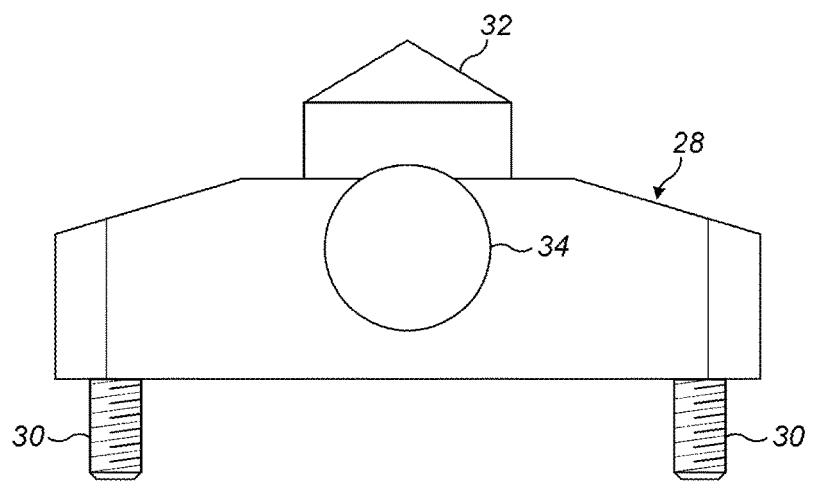
FIG. 3c is an enlarged view of part of the detector holder in accordance with another aspect of the invention.

FIG. 3a is similar to the view in FIG. 2, but shows the detector holder 22 in more detail; the detector holder of FIG. 3a is shown enlarged in FIG. 3b. The detector holder 22 comprises an arm 24 which holds at each end a detector 26 for measuring radiation dose; between the detectors 26 is mounted a marker device 28 which is shown in more detail in the cross-sectional view of FIG. 3c. The marker device 28 comprises a plastic block provided with two pins 30 whereby the marker device can be mounted accurately to matching holes in the arm 24, and it is formed with a conical pointer 32 on the side opposite the pins 30. Inside the block is a radio-opaque marker 34, such as the marker balls described in our earlier European patent application, EP2996614, which can be imaged both by the EPID and the MR imaging apparatus. Forming the block 28 around the marker 34 holds the marker in a fixed spatial relationship to the tip of the cone 32 (in marker devices we have made as shown, the centre of the marker 34 is 12 mm vertically below the tip of the cone 32), and the arm 24 holds the detectors 26 in fixed spatial relationships to the marker 34 and the tip of the pointer 32.

Conventional water tanks have a single detector placed on a moveable arm within the tank (usually with a second detector positioned away from the radiation beam to use as a reference detector). The apparatus for moving the detector holder is attached to the side of the water tank, increasing the overall dimensions of the tank still further. Because of the constrictions of the bore, such an apparatus would not be able to reach the edges of the tank because the motor would hit the top of the bore before the detector got to the tank edges. Therefore we have a detector holder 22 which has two detectors, one at each end of the arm, so they are distanced from the central part of the arm which is mounted to the moving mechanism 20. In operation, this means each edge of the tank can be reached by one or other of the detectors. The dimensions of the detector holder 22 are such that the measurement areas of each detector overlap in the middle, meaning we can make sure the two detectors are matched in order to provide consistent measurements across the whole radiation field. In some cases (as will be described in connection with FIG. 4) they are also offset height-wise too, as the same problems exist when raising the detector holder 22 towards the top of the bore and lowering the detector holder 22 towards the bottom of the tank.

Alignment of the tank 16 within the bore 10 for dose distribution measurement will now be described. The tank 16 is aligned centrally to the central axis of the radiation beam 12 using five radio-opaque markers (e.g. ball bearings) placed on the base of the tank (these must be taken out before the MR imaging apparatus is actuated); alternatively, markers such as those in EP2996614 may be embedded in the material of the base of the tank 16, as they are suitable for use with an operating MRI. One marker is placed in the middle of the tank and four along each major radiation axis. Images of the 5 radiopaque markers, such as X-ray captured by the EPID 15 with the beam 12 directed vertically downwards (or upwards), are analysed to provide lateral (LR), longitudinal (FH) and rotational (around the AP axis) alignment of the tank relative to the radiation centre. The tank 16 is moved and/or rotated in these directions by the couch 10 in the FH direction and by any suitably precise means in the other directions as will be appreciated by those skilled in the appropriate field. We place the tank 16 on an adjustable platform (not shown) which is indexed to the couch 10 and can move the tank laterally and rotationally. Some movement of the tank vertically can be provided for by the couch 10, but is not generally necessary as the tank is used when filled with water, and the depth of the water can be varied as will be described below. Coarse adjustments are made so that the arm 22 is roughly central to the tank 16 and the tank 16 is roughly central to the bore 10, and therefore roughly central to the radiation isocentre. The radiotherapy apparatus 6 is then turned on and is rotated around the bore 10, the beam 12 being turned on at several angles, with images of the beam 12 being recorded by the EPID imager 15 on the opposite side of the bore 10. These images can then be analysed to determine where the marker 34 is in relation to the radiation isocentre (this is essentially a Winston-Lutz test). The position of the marker 34 can then be finely adjusted using the mechanism 20 (which in this case is accurate to 0.1 mm) to place it at the radiation beam isocentre.

Once the marker 34 has been accurately placed at the isocentre, then the tip of the pointer 32 can be placed at the isocentre by moving the detector holder the known distance and direction between the marker and the tip of the pointer 34; the system can then set the pointer position as being at the reference point (0, 0, 0), and then the mechanism 20 can move the arm 24 and the pointer 32 so that it is at the desired water level in the tank 16. Water is then added to or drained from the tank 16 via the tap 23 until the surface of the water and the tip of the pointer 32 are at the same level. In this way we know the height of the surface of the water in the tank to a high degree of accuracy—far higher than the conventional method of placing a sheet of paper on top of the water and reading the ODI. This also means we can change the surface level very accurately, by moving the pointer 32 and adjusting the water surface to it. When taking dose distribution measurements, one detector 22 is placed at the isocentre and referenced at (0, 0, 0) in the same way as the marker 34, and then moved to take measurements at the desired locations; if it is necessary to use the other detector to measure at some locations within the tank then it is referenced and then moved to position in the same way.

As described above, the radiotherapy apparatus is used in the vertical (gantry angle 0° or 180°) and transverse (gantry angle 90° or 270°) positions for taking dose distribution measurements, and in the transverse position the tank 16 is aligned so that the beam 123 is directed so as to pass through one of the windows 18.

Figure 4:
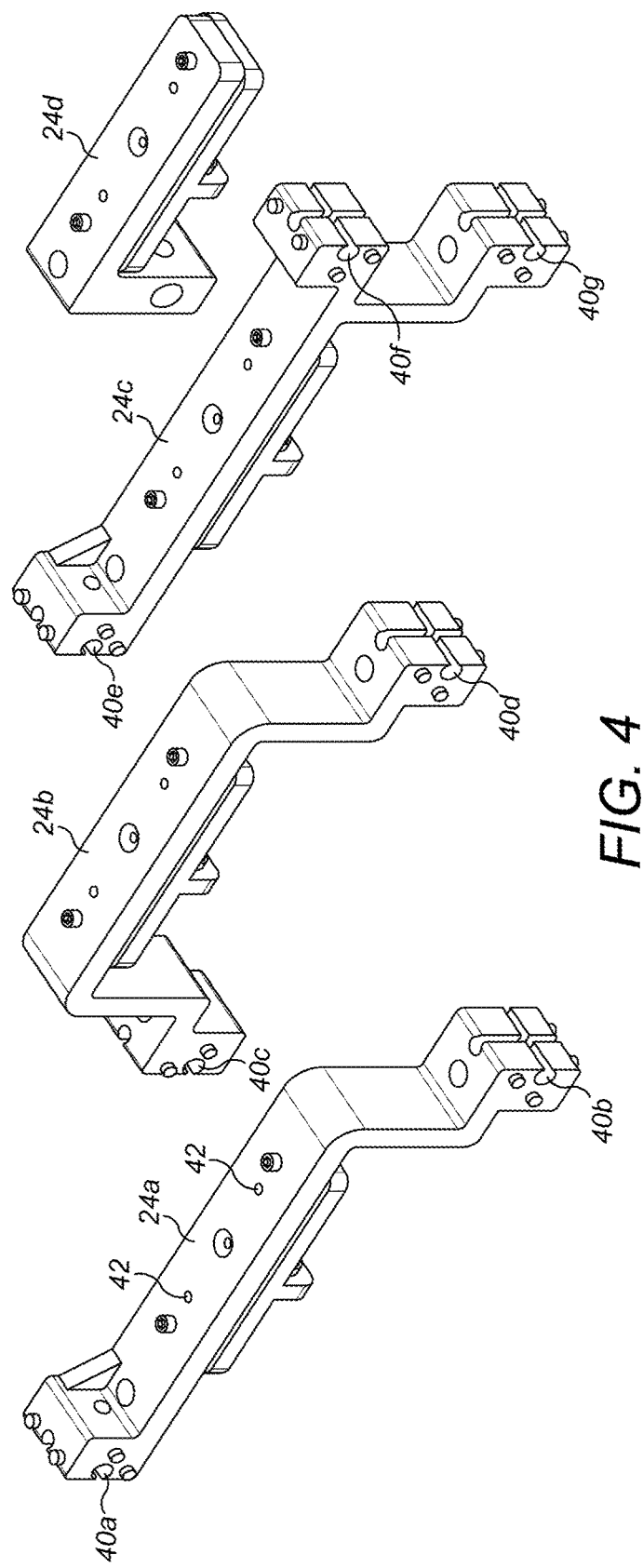
FIG. 4 shows different configurations for the detector holder of FIGS. 3a and 3b.

FIG. 4 shows several different configurations for the detector arm 24. Going from left to right: the first arm 24a has mounts 40a, 40b to releasably receive two detectors (not shown) and is configured so that they are spaced both transversely and vertically, with one mount 40a being vertically aligned with but transversely spaced from the marker (not shown, but the pins 30 would engage in holes 42); the second arm 24b has mounts 40c, 40d to receive two detectors which are vertically aligned with each other but vertically and transversely spaced from the marker; the third arm 24c has three mounts 40e, 40f, 40g to mount two detectors vertically aligned with the marker and a third detector vertically spaced from the marker, and the fourth arm 24d is for mounting only a marker 28.

It will of course be understood that many variations may be made to the above-described embodiment without departing from the scope of the present invention. For example, if the tank and all attachments were MR-compatible then the position of the marker (and hence the position of the detectors) could be monitored during dose distribution measurement by the MR imager. Although described above in connection with an MRL, the present invention may be applied in any radiological apparatus having a central bore, such as a PET apparatus—or indeed in any radiological apparatus which has tight space constraints and limited visibility, and not necessarily a central bore, and the term "bore" used herein and in the claims should be interpreted accordingly. Alignment of the tank is described above using five radio-opaque markers, but this alignment can be performed using only four or even three markers, as those skilled in the art appreciate. It will be appreciated also that the tank could be inserted in the bore while containing no liquid, and the liquid could be added after the tank is located in the bore. Where different variations or alternative arrangements are described above, it should be understood that embodiments of the invention may incorporate such variations and/or alternatives in any suitable combination or variation.

The invention claimed is:

1. A tank configured for placement within a bore of a radiotherapy apparatus, the tank comprising:

a wall extending in a vertical direction, wherein a height of the tank in the vertical direction is less than dimensions of the tank in a plane transverse to the vertical direction, wherein the wall has a substantially constant thickness, and wherein the wall comprises a first section which is substantially thinner than the substantially constant thickness, and a detector holder located at least partially within the tank.

2. The tank according to claim 1, wherein the detector holder comprises:

a radiation detector;

a radio-opaque marker; and a visual reference point, the detector, the marker and the reference point being spatially fixed relative to each other.

3. The tank according to claim 2, wherein the radio-opaque marker is embedded within the detector holder.

4. The tank according to claim 2, wherein the detector is releasably mounted to the detector holder.

5. The tank according to claim 2, wherein the reference point is the point of a conical pointer.

6. The tank according to claim 2, further comprising two detectors mounted to the detector holder, the two detectors being separated horizontally.

7. The tank according to claim 6, further comprising a third detector mounted to the detector holder, the third detector being vertically separated from the two horizontally-separated detectors.

8. The tank according to claim 2, further comprising two detectors mounted to the detector holder, the two detectors being separated vertically.

9. The tank according to claim 1, wherein the wall further comprises a second section which is substantially thinner than the substantially constant thickness, the first and second sections being aligned on opposite sides of the tank.

10. The tank according to claim 1, wherein the wall is formed of optically transparent material.

11. The tank according to claim 1, wherein the tank further comprises an open top, and wherein the detector holder is situated upon an edge of the top.

12. The tank according to claim 1, wherein the tank further comprises a water source attachment situated upon a portion of the wall.

13. The tank according to claim 1, further comprising a fiducial phantom situated on or in the tank, the phantom including a plurality of imaging markers.

14. The tank according to claim 1, wherein the detector holder is further configured to move a detector relative to the radiotherapy apparatus while the radiotherapy apparatus emits radiation in a plurality of directions, the detector being configured to collect radiation dose measurements at different locations within the bore.

* * * * *